United States Patent
Saunders et al.

(10) Patent No.: US 7,292,330 B2
(45) Date of Patent: Nov. 6, 2007

(54) WAFER INSPECTION WITH A CUSTOMIZED REFLECTIVE OPTICAL CHANNEL COMPONENT

(75) Inventors: Winston A. Saunders, Hillsboro, OR (US); James S. Clarke, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 11/332,195

(22) Filed: Jan. 12, 2006

(65) Prior Publication Data

US 2006/0119841 A1    Jun. 8, 2006

Related U.S. Application Data

(62) Division of application No. 10/956,288, filed on Sep. 30, 2004, now abandoned.

(51) Int. Cl.
*G01N 21/88* (2006.01)
*G02B 21/06* (2006.01)
*H01J 3/14* (2006.01)

(52) U.S. Cl. ............ 356/237.2; 250/216; 358/385; 382/281

(58) Field of Classification Search .. 356/237.1–237.6; 250/216, 201.3, 201.4, 201.5, 201.8; 359/385, 359/389, 368, 618–619, 227, 230
See application file for complete search history.

(56) References Cited

U.S. PATENT DOCUMENTS

| | | |
|---|---|---|
| 5,506,676 A | 4/1996 | Hendler et al. |
| 5,587,832 A | 12/1996 | Krause |
| 5,623,281 A | 4/1997 | Markandey et al. |
| 5,796,508 A | 8/1998 | Suzuki |
| 5,923,466 A | 7/1999 | Krause et al. |
| 6,060,224 A * | 5/2000 | Sweatt et al. ............... 430/395 |
| 6,248,988 B1 | 6/2001 | Krantz |
| 6,375,903 B1 * | 4/2002 | Cerrina et al. ............. 422/131 |
| 6,399,935 B1 | 6/2002 | Jovin et al. |
| 6,560,020 B1 * | 5/2003 | Kramer ...................... 359/569 |
| 6,753,947 B2 * | 6/2004 | Meisburger et al. ......... 355/69 |
| 6,788,210 B1 | 9/2004 | Huang et al. |
| 6,870,554 B2 * | 3/2005 | Jain .......................... 345/697 |
| 6,870,659 B2 | 3/2005 | Aubuchon |

(Continued)

OTHER PUBLICATIONS

Winston, A. Saunders, et al., "Wafer Inspection With A Customized Reflective Optical Channel Component" U.S. Appl. No. 10/956,288, Confirmation No. 7041, filed Sep. 30, 2004, Office Action dated Feb. 28, 2006, pp. 1-13.

(Continued)

*Primary Examiner*—Sang H. Nguyen
(74) *Attorney, Agent, or Firm*—Blakely, Sokoloff, Taylor & Zafman LLP

(57) ABSTRACT

A method is described that adjusts the position of a item and sets a tilt angle for each of a plurality of micro-mirrors of a digital micro-mirror device. The setting of the tilt angles is to establish a filter within the optical channel of an inspection tool that inspects the item. The filter is to reduce noise received at an optical detection device. The tilt angle settings are a function of the position. The method also includes comparing information from the optical detection device that describes an inspected region of the item's surface against an expected version of the information.

6 Claims, 5 Drawing Sheets

U.S. PATENT DOCUMENTS 6,898,004 B2 * 5/2005 Shimizu et al. ............ 359/385
6,922,483 B2 * 7/2005 Doane ....................... 382/149
7,119,940 B2 * 10/2006 Knipe ........................ 359/290

OTHER PUBLICATIONS

Winston, A. Saunders, et al., "Wafer Inspection With A Customized Reflective Optical Channel Component" U.S. Appl. No. 10/956,288, Confirmation No. 7041, filed Sep. 30, 2004, Final Office Action dated Jul. 28, 2006, pp. 1-12.

Dudley, D., et al., "Emerging Digital Micromirror Device (DMD) Applications", SPIE Proceedings, vol. 4985;2003, pp. 12, DLP Texas Instruments, Inc., Society of Photo-Optical Instrumentation Engineers.

Liang, M., et al., Cofocal pattern period in multiple-aperture confocal imaging systems with coherent illumination, Jun. 1, 1997, Optics Letter, vol. 22, No. 11, pp. 751-753.

Macaulay, C., et al. "Use of digital micro mirror devices in quantitative microscopy," Proc. SPIE, vol. 3260, 1998, p. 201-206.

Dlugan, A.L.P., et al. "Improvements to quantities microscopy through the use of digital micromirror devices," Proc. SPIE 3221, pp. 6-11, 2000.

Hanley, Q.S., et al., An optical sectioning programmable array microscope implemented with a digital micromirror device, Journal of Microscopy, vol. 196, Pt.3;1999; pp. 317-331.

Wagner, E.P., "Construction and Evaluation of a Visible Spectrometer Using Digital Micromirror Spatial Light Modulation", Applied Spectroscopy, vol. 49, No. 11, pp. 1715-1719, 1995.

Deverse, R.A., et al., "Realization of the Hadamard Multiplex Advantage using a Programmable Optical Mask in a Dispersive Flat-Field near-Infrared Spectrometer," Applied Spectroscopy, vol. 54, No. 12, 2000, pp. 1751-1758.

Dudley, D. et al., "Emerging Digital Micromirror Device (DMD) Applications", Texas Instruments, Inc., pp. 10, publicly available not later than Sep. 29, 2004.

Hornbeck, L., "Digital Light Processing™: A New MEMS-Based Display Technology", Texas Instruments, pp. 18, publicly available not later than Sep. 29, 2004.

Douglass, M.R., "Lifetime Estimates and Unique Failure Mechanisms of the digital Micromirror Device (DMD)", Texas Instruments, Digital Imaging, pp. 12, publicly available not later than Sep. 29, 2004.

Hornbeck, L., "Current Status and Future Applications for DMD™-Based Projection Displays", Texas Instruments, Digital Imaging, pp. 4, publicly available not later than Sep. 29, 2004.

Yoder, L, "The Digital Display Technology of the Future", pp. 1-11, DLP A Texas Instruments Technology, Jun. 5-7, INFOCOMM 1997.

A.L.P. Dlugan, C.E. MacAulay and P.M. Lane, "Improvements to quantitative microscopy through the use of digital micromirror devices," Proc. SPIE 3921, pp. 6-11. 2000.

J.B. Sampsell, "The Digital Micromirror Device and Its Application To Projection Displays," Texas Instruments, Inc., Microelectronics and Nanometer Structures, 1994, vol. 12, No. 6, p. 3252-6, May-Jun. 1994, IEEE, Op. Soc. America.

* cited by examiner

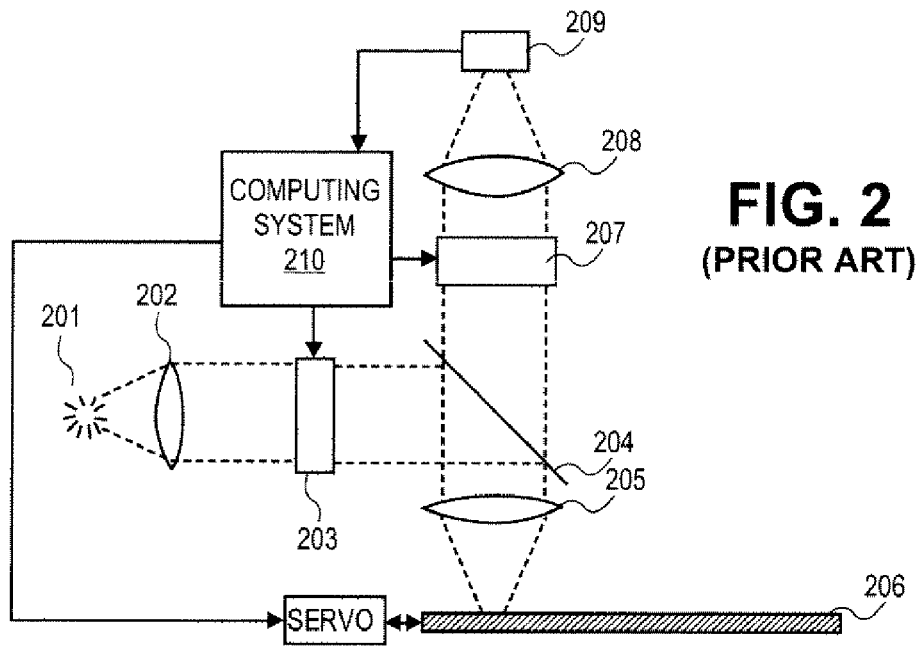
FIG. 2
(PRIOR ART)
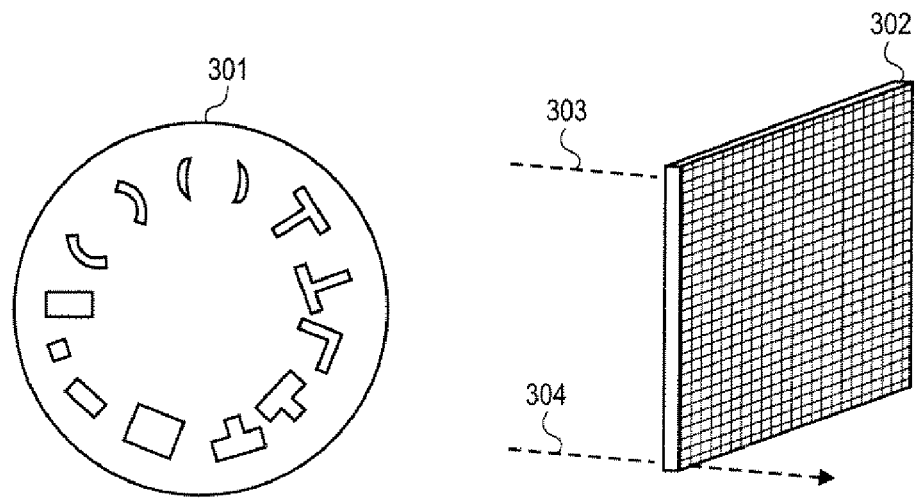
FIG. 3A
(PRIOR ART)
FIG. 3B
(PRIOR ART)

WAFER INSPECTION WITH A CUSTOMIZED REFLECTIVE OPTICAL CHANNEL COMPONENT

This application is a divisional application and claims the priority date of U.S. patent application Ser. No. 10/956,288, filed Sep. 30, 2004 now abandoned entitled, Wafer Inspection With A Customized Reflective Optical Channel Component.

FIELD OF INVENTION

The field of invention relates generally to wafer inspection, and, more specifically, to wafer inspection with a customized reflective optical channel component.

BACKGROUND

In the semiconductor arts multi-layer structures are created upon semiconductor wafers that comprise electrically conductive lines and vias surrounded by one or more electrically insulating dielectric layers. The lines, vias and dielectric layers may be said to be "pattered" into specific structures that implement specific circuitry. Because the dimensions of these patterns can be extremely small (e.g., current mass production technologies can reduce features to as small as 90 nm across), the impact of a manufacturing defect is becoming more important as is the difficulty in detecting it.

In order to detect manufacturing defects optically, a spot of light is focused on a region of the wafer's patterned structures. The reflected image of the patterned structure is captured through an optical channel and resolved on an optical detection device such as a photodetector or charge coupled device (CCD). Data produced by the optical detection device is then compared against "expected data"; where, the expected data corresponds to the data from the optical detection device if the manufactured patterns illuminated by the focused spot of light were properly manufactured.

FIGS. 1a and 1b demonstrate a problem that exists with respect to the optical detection of a manufacturing defect. FIG. 1a shows an example of a "noiseless" optical signal that is resolved to the optical detection device; and, FIG. 1b shows an example of a "noisy" optical signal that is resolved to the optical detection device. Spot 101a corresponds to the illuminated spot of light that is focused on the wafer's structural patterns. As a simple example, the wafer's structural patterns are shown to include a repeating pattern of conductive lines $102_1$ through $102_5$ separated by a dielectric material region (which is drawn in FIG. 1a as a shaded region).

Looking along axis 104, a one-dimensional signal 107 should be resolved upon the optical detection device. Assuming the conductive lines have higher reflectivity of the focused spot of light than the dielectric material, enhanced optical intensity should be observed at the detector for the conductive lines as compared to the dielectric regions. Signal 107 indicates as much through optical intensity spikes $105_1$ through $105_5$ which are meant to correspond to conductive lines $102_1$ through $102_5$, respectively.

A manufacturing defect 103 is also observed in the image 101a of FIG. 1a. This manufacturing defect may be the result of a thin layer of "spilled" conductive material, a "pit" or "void", etc. Whatever its form, the defect ultimately reproduces on the optical detection device as part of signal 107 with an intensity 106 that is less than the intensity of the spikes $105_1$ through $105_5$ that are associated with the conductive lines $102_1$ through $102_5$.

FIG. 1b shows an image 101b of the same region of the same wafer as depicted in FIG. 1a, but with noise attributed to complications that arise from the optical processing of the reflected image from the wafer. Specifically, because the patterned structures on the wafer are "three dimensional" in the sense that the conductive lines $102_1$ through $102_5$ have "edges" that determine the lines' thickness, the light that reflects off of the wafer does not reflect uniformly off of the wafer surface. For example, a ray of light that impinges directly upon a flat portion of a conductive line may reflect perpendicular to the surface of the wafer while a ray of light that impinges at an edge of a conductive line may reflect at an angle other than perpendicular with the wafer surface (i.e., the angle of reflection is different for rays that impinge upon flat conductive line surfaces as opposed to conductive line edges).

As processed by the optical channel between the wafer and the optical detection device, the various components of light that reflect off of the wafer at varying angles depending on surface topography (and intensity depending on reflectivity) may constructively or de-constructively interfere so as to create bright or dark "noise" spots in the signal that is resolved on the optical detection device. FIG. 1b shows such a bright noise spot 108 (also referred to as a "lobe") that might result, for instance, from the constructive interference of light reflected off of the edges of the conductive lines.

The portion 111 of the resolved signal 110 that corresponds to the lobe 108, being a deviation from the noiseless signal 107, corresponds to an item of noise that makes detection of the defect difficult or impossible. For example, with the lobe 108 being positioned around the defect itself, the resolved signal superimposes the intensity spikes 112, 113 that correspond to conductive line 1024 and defect 103, respectively. At a minimum, owing to the intensity 111 of the lobe, it will more difficult to detect the signal from the defect 113 in FIG. 1b as compared to the signal from defect 106 observed in FIG. 1a. In an extreme case, if the lobe's intensity is beyond the saturation level 114 of the optical detector device, the defect will be impossible to detect (because the data from the optical detection device will clip at level 114).

FIGURES

The present invention is illustrated by way of example and not limitation in the figures of the accompanying drawings, in which like references indicate similar elements and in which:

FIG. 2 shows a design for a wafer inspection tool;

FIG. 3a shows an aperture wheel;

FIG. 3b shows a liquid crystal array;

DESCRIPTION

Figure 1A:
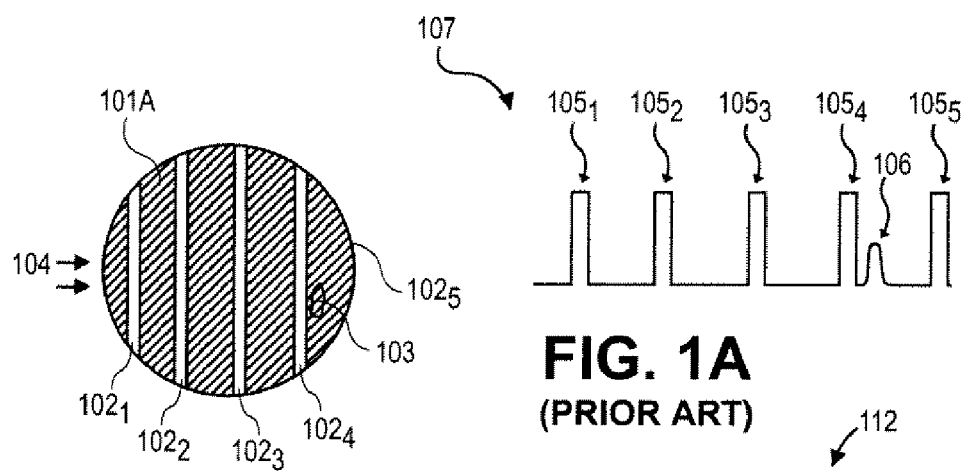
FIG. 1a shows a noiseless image for wafer defect inspection and a corresponding signal along a particular axis.

In order to address noise problems that result from the varying of reflective angles and reflectivity from a three dimensional patterned structure, engineers have attempted to impose filters in the optical processing channel used for optical defect detection. FIG. 2 shows a depiction of an imaging system for detecting defects on a wafer 206. A light source (e.g., a laser) 201 emits light that is collected by a lens 202. The collected light travels through a filter 203 which filters the light as described in more detail further below.

The filtered light impinges upon a beam splitter 204 which directs the light toward the wafer 206 surface. The light from the beam splitter 204 is focused into a "spot" on the wafer 206 by a focusing lens 205. The patterned features of the wafer 206 that are illuminated beneath the spot correspond to the features that are being inspected for a defect. Typically, the wafer 206 can be moved beneath the spot so that after a first region of the wafer is inspected, second and subsequent wafer regions can be inspected by adjusting the wafer position for each region to be inspected.

The light that is reflected from the wafer surface is collected and directed toward the optical detection device 209 (e.g., photodetector, charge coupled device (CCD) array, etc.). Along the optical channel between the wafer 206 and the optical detection device 209, another filter 207 may exist (or, filter 207 may exist and filter 203 may not exist). The filters are configured to affect the light so as to reduce the noise that may be resolved onto the optical detection device 209.

Figure 1B:
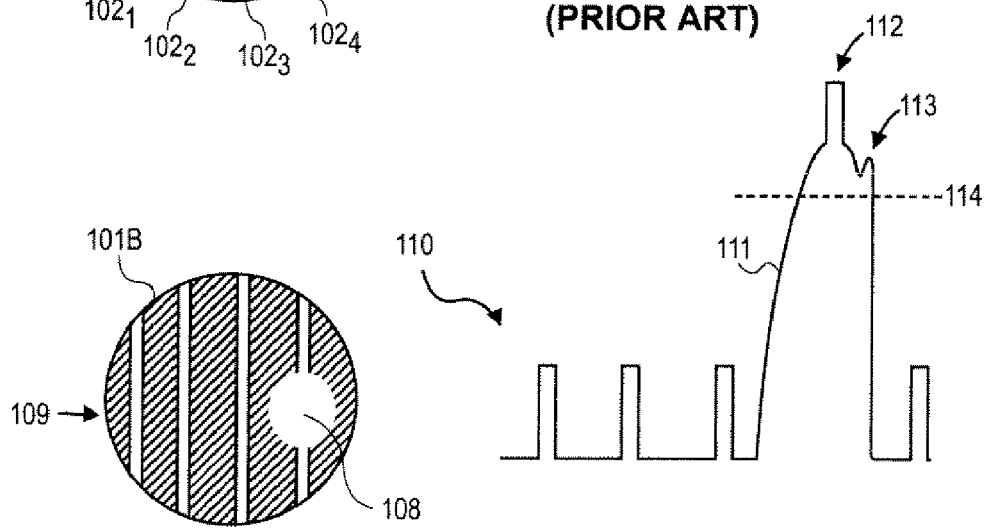
FIG. 1b shows an exemplary noisy image for the wafer defect inspection of FIG. 1a and a corresponding signal along the same axis.

For example, considering the problem discussed above with respect to FIG. 1b, filter 203 may be configured to filter out specific regions of light that that impinge on a conductive line edge and constructively interfere with other light (i.e., an attempt is made to filter out light that contributes to lobe 108, 111 prior to focusing onto wafer 206). Likewise, filter 207 may be configured to filter out specific regions of light that would otherwise constructively interfere with one another to form lobe 108, 111 upon the optical detector 209. By filtering out light that contributes to noise, the resolved signal at the detector will approach a "noiseless" signal (e.g., as depicted in FIG. 1a) so as to make defect inspection easier.

Because each different region of the wafer that is inspected is expected to have "its own" patterned structure, and because the noise produced from reflected light is expected to exhibit differing features for differing patterned structures, the noise to be filtered out "changes" as a function of wafer position. For example, a first wafer region having conductive lines oriented along a "z" axis might produce a lobe at first position within the reflected image; while, a second wafer region having conductive lines oriented along an "x" axis might produce a lobe at a second position within the reflected image. The filtering profile of filters 203, 207 must therefore be specially configured for each wafer position.

Filters 203, 207 are therefore ideally capable of imposing different filtering characteristics that can be precisely specified. FIG. 2 indicates that a computing system 210 which controls the wafer position is also used to set the filtering profile of each of the filters 203, 207. Here, the expected patterned structure beneath the focused light—and its corresponding noise—is known prior to the testing of the wafer 206. As such, the computing system 210 can be programmed with the proper filtering profiles for each wafer position so that the noise that is created at each wafer position can be diminished at least to some degree.

FIGS. 3a and 3b show different types of filters that have been used for the filters 203, 207 discussed above. FIG. 3a shows an aperture wheel 301 and FIG. 3b shows a liquid crystal array 302. The aperture wheel has a collection of different apertures around its circumference that each act as a filter having a specific filtering profile. Light is passed through a specific aperture by rotating the wheel such that the specific aperture is rotated into the light path.

FIG. 3b shows an array 302 of liquid crystals. Each liquid crystal in the array 302 can have its optical transmissivity individually set (e.g., to pass light or to not pass light). For example as depicted in FIG. 3b, the upper left liquid crystal in the array 302 is configured to not pass its incident light whereas the lower left liquid crystal in the array 302 is configured to pass its incident light.

A problem with the aperture wheel is that the number of apertures, and therefore the number of different filtering profiles that can be effected, is limited. The liquid crystal array 302, although capable of a multitude of different filtering profiles owing to the discrete transmission control of its constituent liquid crystals, is expected to be less and less "workable" as the wavelength of the light from light source 201 is reduced in the coming years into the deep ultra violet (DUV) spectrum (so as to enable the detection of smaller wafer pattern features). Presently known liquid crystals are either highly absorptive or reflective in the DUV spectrum and therefore do not posses the transmission qualities for effecting a transmission filter as described just above with respect to FIG. 3b.

A solution to these problems is to use a digital micromirror device (DMD) as a noise filter in an inspection tool. A DMD is an arrangement (e.g., an array) of small mirrors ("micro-mirrors"), where the tilt angle of each micro-mirror in the arrangement is capable of being individually set with digital information that is directed toward the DMD. Examples of DMDs include DLP™ DMDs from Texas Instruments, Inc. Because many materials are known to be reflective in the DUV spectrum, a DMD coated with one or more materials that are suitably reflective in the DUV spectrum should not experience a functional roll-off in the DUV spectrum as with liquid crystal arrays.

Moreover, because the tilt angle can be individually set for each mirror in the arrangement, the reflectivity of the DMD surface as a whole can be configured into a number of different filtering profiles. As such, the filtering profile variability associated with liquid crystal arrays is at least somewhat preserved but with workable functionality at least in the DUV spectrum. Even though aperture wheels are workable in the DUV spectrum, the limited selection of filtering profiles that is attainable with an aperture wheel should make a DMD based filter a better solution for filtering out the different types of noise profiles that may need to be filtered over the lifetime of the inspection tool.

Figure 4:
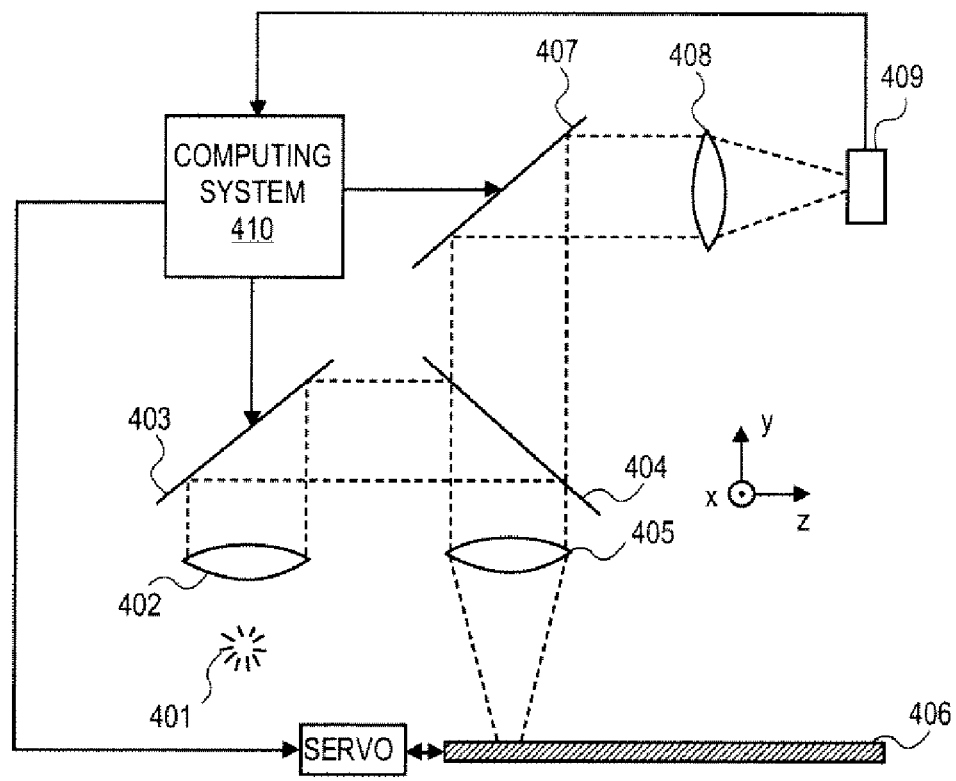
FIG. 4 shows a wafer inspection tool that employs a digital micromirror device (DMD) as a filter.

FIG. 4 shows a wafer inspection tool that employs DMD filters 403, 407. A light source (e.g., a laser, a lamp, etc.) 401 emits light that is collected by a lens 402. The collected light travels through a DMD filter 403 which filters the light as described in more detail further below.

The filtered light impinges upon a beam splitter 404 which directs the light toward the wafer 406 surface. The light from the beam splitter 404 is focused into a "spot" on the wafer 406 by a focusing lens 405. The patterned features of the wafer 406 that are illuminated beneath the spot correspond to the features that are being inspected for a defect. Like the system shown on FIG. 2, the wafer 406 can be moved beneath the spot so that after a first region of the wafer is inspected, second and subsequent wafer regions can be inspected by adjusting the wafer position for each region to be inspected.

The light that is reflected from the wafer surface is collected and directed toward the optical detection device 409. Along the optical channel between the wafer 406 and the optical detection device 409, another filter 407 may exist (or, filter 407 may exist and filter 403 may not exist). Like the system in FIG. 2, the filters are configured to affect the light so as to reduce the noise that may be resolved onto the optical detection device 409. However, unlike the system of FIG. 2, the filters 403, 407 use reflection—rather than transmission—as the mechanism by which light is passed through the channel.

Figure 5A:
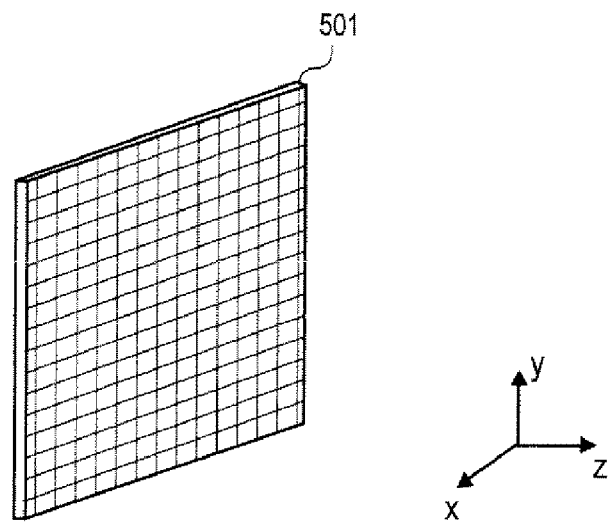
FIG. 5a shows a first perspective of a DMD.
Figure 5B:
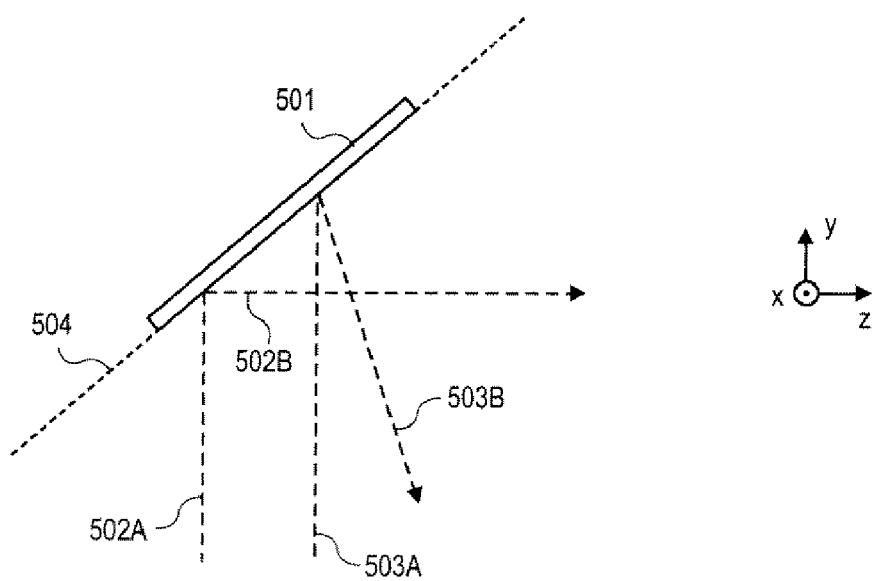
FIG. 5b shows a second perspective of a DMD.

FIGS. 5*a* and 5*b* explore this aspect in more detail. FIG. 5*a* shows the surface of a DMD device 501. Note that the DMD surface is pixilated similar to that of a liquid crystal display. However, each pixel corresponds to a reflective mirror rather than a transmissive liquid crystal. Because the tilt angle of each mirror can be individually set, a first tilt angle can be used to reflect light so that it continues into the optical channel that is used to inspect the wafer; while, a second tilt angle can be used to reflect light so that it is reflected out of the optical channel that is used to inspect the wafer. Therefore, in order to establish a specific filtering profile, the mirrors that receive the regions of light that are intended to be filtered out are set to the second tilt angle; and, the mirrors that receive the regions of light that are not intended to be filtered out are set to the first tilt angle.

FIG. 5*b* shows an example. The DMD device 501 of FIG. 5*a* is shown oriented in FIG. 5*b* at an angle that conforms to the position of DMD filter 403 of FIG. 4. Here, a tilt angle of 0° relative to the plane 504 of the DMD device 501 (i.e., a micro-mirror with its reflective surface lying along plane 504) corresponds to a micro mirror being positioned to reflect its light into the optical channel. More specifically, referring to FIGS. 4 and 5*b*, the plane of DMD filter 403, 501 is oriented 45° relative to the z axis. As a consequence, any micro mirror having a tilt angle of 0° relative to the plane 504 of the DMD filter 403, 501 will cause light 502*a* that is directed along the +y axis from light source 401 to be reflected along the +z axis 502*b* into beam splitter 404. As such, a 0° tilt angle relative to the plane 504 of the DMD filter 403, 501 corresponds to the "first" tilt angle defined above for those regions of light that are not supposed to be filtered out of the optical channel.

By contrast, micro mirrors oriented so as to face more toward the xz plane than the 0° tilt angle faces toward the xz plane will cause light 503*a* that is directed along the +y axis from light source 401 to be reflected 503*b* in the −y direction and out of the optical channel. As such, an orientation that faces more toward the xz plane than the 0° tilt angle corresponds to the "second" tilt angle described above for those regions of light that are supposed to be filtered out of the optical channel. The same analysis discussed above for DMD filter 403 also applies to DMD filter 407.

Therefore specific filtering profiles can be established simply by setting to a first tilt angle those micro-mirrors that receive light that is not supposed to be filtered out; and, setting to a second tilt angle those micro-mirrors that receive light that is supposed to be filtered out.

Similar to the discussion provided above with respect to the system shown in FIG. 2, because each different region of the wafer that is inspected is expected to have "its own" patterned structure, and because the noise produced from reflected light is expected to exhibit differing features for differing patterned structures, the noise to be filtered out "changes" as a function of wafer position. For example, a first wafer region having conductive lines oriented along the "z" axis might produce a lobe at first position within the reflected image; while, a second wafer region having conductive lines oriented along an "x" axis might produce a lobe at a second position within the reflected image. The filtering profile of filters 403, 407 must therefore be specially configured for each wafer position.

Because each of the micro-mirrors of DMD filters 403, 407 are capable of being individually adjusted the DMD filters 403, 407 are capable of imposing different filtering characteristics that can be precisely specified. FIG. 4 indicates that a computing system 410 which controls the wafer position is also used to set the filtering profile of each of the DMD filters 403, 407 through the individual adjustment of their respective micro-mirrors (e.g., for each of the DMD filters 403, 407, a first group of micro mirrors are set to the above described "first" tilt angle and a second group of micro mirrors are set to the above described "second" tilt angle.

Here, as with the system in FIG. 2, the expected patterned structure beneath the focused light—and its corresponding noise—is known prior to the testing of the wafer 406. As such, the computing system 410 can be programmed with the proper filtering profiles for each wafer position so that the noise that is created at each wafer position can be diminished at least to some degree.

Figure 6:
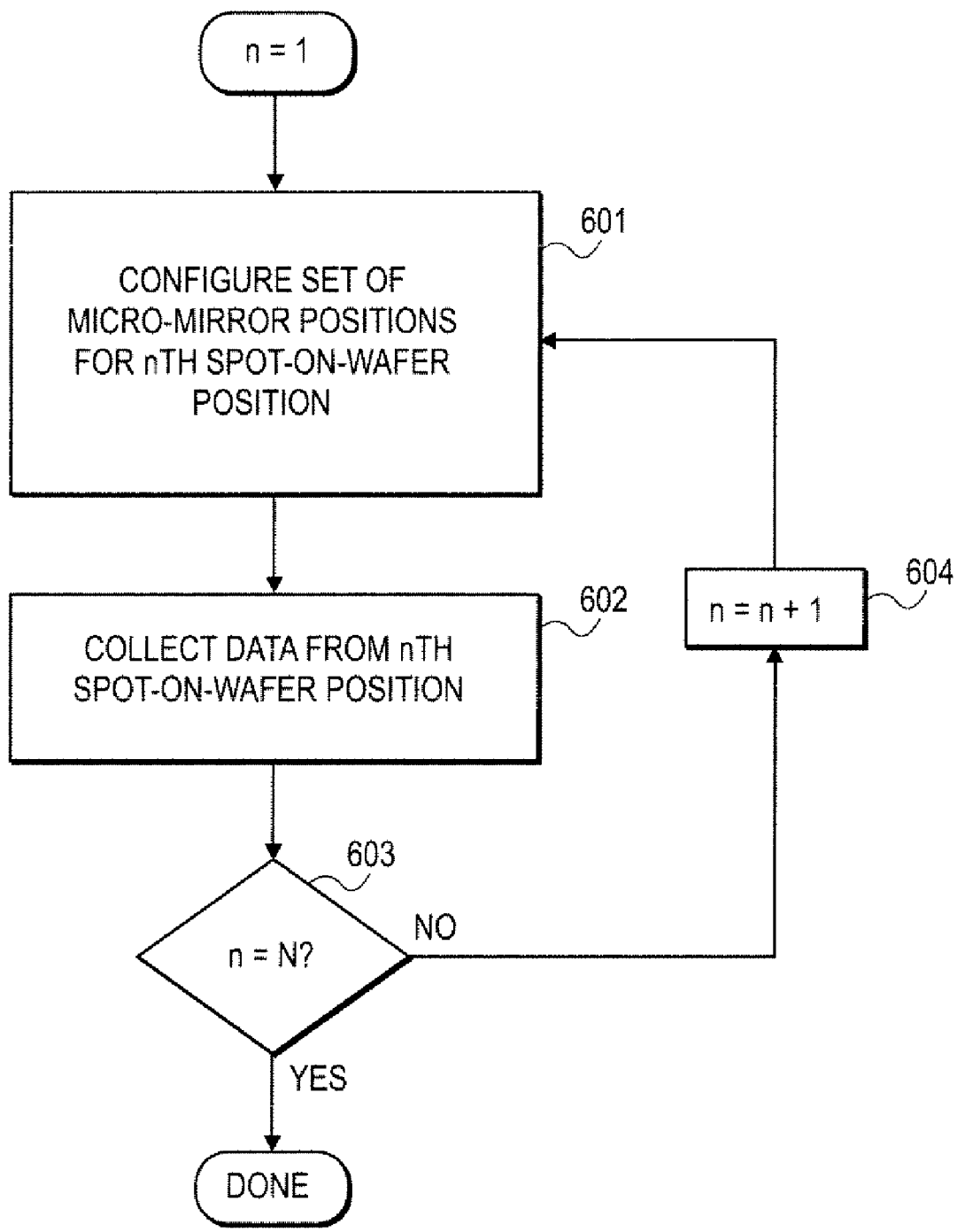
FIG. 6 shows a methodology that can be performed by the wafer inspection tool of FIG. 4.

FIG. 6 shows a wafer inspection process that can be executed by the system observed in FIG. 4. The wafer inspection process may be implemented, at least in one embodiment, as program code that is executed upon the processing core of the computing system 410. According to the process of FIG. 6, a set of micro-mirror positions are configured for a particular (nth) position on the wafer onto which the inspection light is focused 601. If the system comprises two DMD filters (as observed in FIG. 4), the set includes the positions for both of the DMD filters.

In an embodiment, a first group of the set are configured to a first tilt angle that keeps light within the optical channel and a second group of the set are configured to a second tilt angle that reflects light out of the optical channel. The first DMD filter's first group and second group combination defines the first DMD filter's filtering profile. The second DMD filter's first group and second group combination defines the second DMD filter's filtering profile.

The filtering should at least reduce to some degree the noise that is resolved to the optical detection device. The data from the optical detection device is collected 602 and, at some point, compared to data that represents the expected image at the nth wafer position. Deviations from the expected image and the collected data image are used to flag manufacturing defects. At least after the data is collected for the nth position wafer position, the wafer position is changed so that the focused light impinges upon the next wafer at a next wafer position 604 out of N total wafer positions 603.

It should be noted that although the context of the above description has been directed to patterned semiconductor wafer inspection, the principles described herein can be applied to any item whose surface is to be inspected.

It is also to be understood that because embodiments of the methods of the present teachings may be implemented as one or more software programs, embodiments of the present teachings may be implemented or realized upon or within a machine readable medium. A machine readable medium includes any mechanism for storing or transmitting information in a form readable by a machine (e.g., a computer).

For example, a machine readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

The invention claimed is:

1. An inspection tool, comprising:
a deep ultra violet light source to emit deep ultra violet light;
an optical detection device to receive deep ultra violet light;
an optical channel through which deep ultra violet light from said deep ultra violet light source travels toward said optical detection device, said optical channel to include an item to be inspected;
a digital micro-mirror device within said optical channel to reduce noise received at said optical detection device, said digital micro-mirror device located along said optical channel between said deep ultra violet light source and said item to be inspected, said digital micro-mirror device having a plurality of micro-mirrors each having its own adjustable tilt angle to be set to one of:
a first position to reflect a portion of said deep ultra violet light into said optical channel;
a second position to reflect a portion of said deep ultra violet light out of said optical channel;
a second digital micro-mirror device within said optical channel to reduce noise received at said optical detection device, said second digital micro-mirror device located along said optical channel between said item to be inspected and said optical detection device, said second digital micro-mirror device also having a plurality of micro-mirrors each having its own adjustable tilt angle, said adjustable tilt angle to be set to:
a third position to reflect a portion of said deep ultra violet light into said optical channel;
a fourth position to reflect a portion of said deep ultra violet light out of said optical channel.

2. The inspection tool of claim 1 further comprising a computing system coupled to said digital micro-mirror device, said computing system having software to determine said positions.

3. A method, comprising:
setting individual positions of micro-mirrors of a digital micro-mirror device to a first set of positions;
setting individual positions of micro-mirrors of a second digital micro-mirror device to a second set of positions;
radiating deep ultra violet light from a deep ultra violet light source;
affecting said deep ultra violet light's propagation direction toward an optical detection device by:
reflecting said deep ultra violet light from said digital micro-mirror device, said first set of positions causing a first portion of said deep ultra violet light to be reflected into an optical channel that flows to an item under inspection and a second portion of said deep ultra violet light to be reflected such that it does not enter said optical channel;
reflecting said first portion of said deep ultra violet light from said item under inspection;
reflecting said first portion of deep ultra violet light from a second digital micro-mirror device, said second set of positions causing a third portion of said first portion of said deep ultra violet light to be reflected into a second optical channel that flows to said optical detection device and a fourth portion of said deep ultra violet light to be reflected such that it does not enter said second optical channel; and,
receiving said third portion of said deep ultra violet light at said optical detection device after said reflecting from said digital micro-mirror device, said reflecting from said item under inspection and said reflecting from said second digital micro-mirror device.

4. The method of claim 3 further comprising comparing first data derived from said optical detection device's response to said receiving against second data, said second data derived from a location on said item where said reflecting of said first portion of said deep ultra violet light from said item occurs.

5. The method of claim 4 where said comparing is performed with a software program being executed on a computing system, said software program also determining said positions.

6. The method of claim 5 further comprising setting individual positions of said micro-mirrors within said digital micro-mirror device to third and fourth sets of positions, said third and fourth sets of positions derived from a second location on said item where reflecting of said deep ultra violet light will occur, said second location different than said location, said first set of positions different than said second set of positions.

\* \* \* \* \*